United States Patent [19]

DeLuca et al.

[11] Patent Number: 4,857,518

[45] Date of Patent: Aug. 15, 1989

[54] HYDROXYLATED 24-HOMO-VITAMIN D DERIVATIVES AND METHODS FOR PREPARING SAME

[75] Inventors: Hector F. DeLuca, Madison, Wis.; Nobuo Ikekawa, Tokyo, Japan; Yoko Tanaka, Delmar, N.Y.

[73] Assignee: Wisconsin Alumni Research Foundation, Madison, Wis.

[21] Appl. No.: 835,065

[22] Filed: Feb. 28, 1986

Related U.S. Application Data

[63] Continuation-in-part of Ser. No. 657,549, Oct. 4, 1984, abandoned.

[51] Int. Cl.$^4$ .......................... A61K 31/59; C07J 9/00
[52] U.S. Cl. ................................... 514/167; 260/397.2
[58] Field of Search ...................... 260/397.2; 514/167

[56] References Cited

U.S. PATENT DOCUMENTS 4,225,596  9/1980  Deluca ........................... 260/397.2
4,448,721  5/1984  DeLuca et al. ................ 260/397.2

*Primary Examiner*—Leonard Schenkman
*Assistant Examiner*—Joseph A. Lipovsky
*Attorney, Agent, or Firm*—Howard W. Bremer

[57] ABSTRACT

This invention is directed to new 24-homo-vitamin D compounds, to methods for preparing the same and novel intermediate compounds.

The compounds are characterized by vitamin D-like activity of the order of $1\alpha,25$-dihydroxyvitamin $D_3$, the recognized circulating hormonal form of vitamin D, or various of its derivatives and by greater antineoplastic activity than such compounds but without their attendant calcemic activity. The compounds are useful in the treatment of disease states characterized by calcium-phosphorous imbalances and where antineoplastic activity is indicated.

10 Claims, No Drawings

HYDROXYLATED 24-HOMO-VITAMIN D DERIVATIVES AND METHODS FOR PREPARING SAME

This application is a continuation-in-part of application Ser. No. 657,549, filed Oct. 4, 1984, now abandoned.

TECHNICAL FIELD

This invention relates to novel vitamin D derivatives.

More specifically, this invention relates to 24-homovitamins.

Still more specifically this invention relates to hydroxylated 24-homovitamins.

Vitamin D is known to regulate calcium and phosphorous metabolism in animals and humans and it has now been firmly established that the biological efficacy of vitamin D depends upon its metabolic conversion, in vivo, to hydroxylated derivatives. Thus vitamin $D_3$ is hydroxylated in vivo to 25-hydroxyvitamin $D_3$ in the liver which in turn is converted into 1α,25-dihydroxyvitamin $D_3$ in the kidneys. It is the latter compound which is now recognized as being the circulating hormonal form of vitamin D.

Because of their biological activity in promoting calcium and phosphorous transport in the intestine and the mobilization and mineralization of bone these forms of vitamin D are important pharmaceutical products which are eminently suitable for use in the treatment of various bone disorders.

BACKGROUND ART

Vitamin D derivatives and their preparation and application are discussed in many references in the patent and other literature. For example, U.S. Pat. No. 3,565,924 is directed to 25-dihydroxycholecalciferol; U.S. Pat. No. 3,657,559 is directed to 1,25-dihydroxycholecalciferol; U.S. Pat. No. 3,741,996 is directed to 1α-hydroxycholecalciferol; U.S. Pat. No. 3,786,062 is directed to 22-dehydro-25-hydroxycholecalciferol; U.S. Pat. No. 3,880,894 is directed to 1,25-dihydroxyergocalciferol; U.S. Pat. No. 4,201,881 is directed to 24,24-difluoro-1α,25-dihydroxycholecalciferol; U.S. Pat. No. 4,196,133 is directed to 24,24-difluoro-1α,25-dihydroxycholecalciferol.

DISCLOSURE OF INVENTION

New derivatives of vitamin $D_3$ have now been found which express excellent vitamin D-like activity and which, for that reason, could readily serve as a substitute for vitamin $D_3$, as well as various of its derivatives, in known applications, such as, for example the treatment of various disease states manifesting calcium and phosphorous imbalance as hypoparathyroidism, osteodystrophy, osteomalacia and osteoporosis.

In addition, these derivatives exhibit an unexpectedly high antineoplastic activity and, also unexpectedly and unpredictably offer such activity without an enhanced calcemic activity. These characteristics would make the compounds eminently suitable as substitutes for certain of the vitamin D derivatives in the treatment of leukemoid disease (see Suda et al, U.S. Pat. No. 4,391,802).

These derivatives are 24-homovitamins and particularly 1α,25-dihydroxy-22E(orZ)-dehydro-24-homovitamin $D_3$ and 1α,25-dihydroxy-24-homovitamin $D_3$.

Compounds of the present invention can be conveniently represented by the formula:

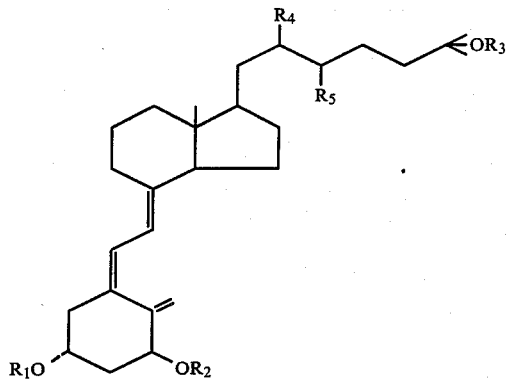

where $R_1$, $R_2$ and $R_3$ are each selected from the group consisting of hydrogen, an acyl group having from 1 to about 4 carbon atoms, and benzoyl and $R_4$ and $R_5$ each represent hydrogen atoms or taken together form a carbon to carbon double bond.

BEST MODE FOR CARRYING OUT THE INVENTION

The compounds of this invention can be prepared in accordance with the process shown in the following schematic and process description. In the schematic and detailed description of the process like numbers identify like compounds.

In accordance with the process of this invention:

Bisnorcholenic acid acetate (a) was reduced with lithium aluminum hydride and subsequently oxidized with dichlorodicyanobenzoquinone to afford the 1,4,6-triene-3-one (b) in 47% yield. The 22-THP-ether of b was treated with alkaline hydrogen peroxide to give the 1α,2α-epoxide (1) in 41% yield. Reduction of (1) with lithium and ammonium chloride in liquid ammonia-tetrahydrofuran at −78°, and subsequent treatment with chloromethyl methyl ether provided the dimethyoxymethyl ether (2) in 38% yield. Removal of the THP group, followed by Swern oxidation gave the aldehyde (4) in 81% yield. This was reacted with vinylmagnesium bromide to provide the allylalcohol (5) in 94% yield. This alcohol was heated in refluxed xylene with triethyl orthoacetate and a catalytic amount of propionic acid, to afford the ester (6) in 93% yield. Then, the ester (6) was reacted with methylmagnesium bromide to provide the alcohol (7) in 93% yield. Removal of MOM group, followed by acetylation gave (22E)-1α,3β-diacetoxy-25-hydroxy-24-homo-cholesta-5,22-diene (9) in 73% yield.

Allylic bromination of (9) with N-bromosuccinimide, followed by treatment with tetra-n-butylammonium bromide and then with tetra-n-butylammonium fluoride gave the 5,7,22-triene (10) as a main product in 24% yield. The 5,7-diene (10) was irradiated with a medium pressure mercury lamp in benzene-ethanol for 5 min, subsequently refluxed for 1 hr, and then hydrolyzed to afford (22E)-1α,25-dihydroxy-22-dehydro-24-homovitamin $D_3$ (11) in 22% yield.

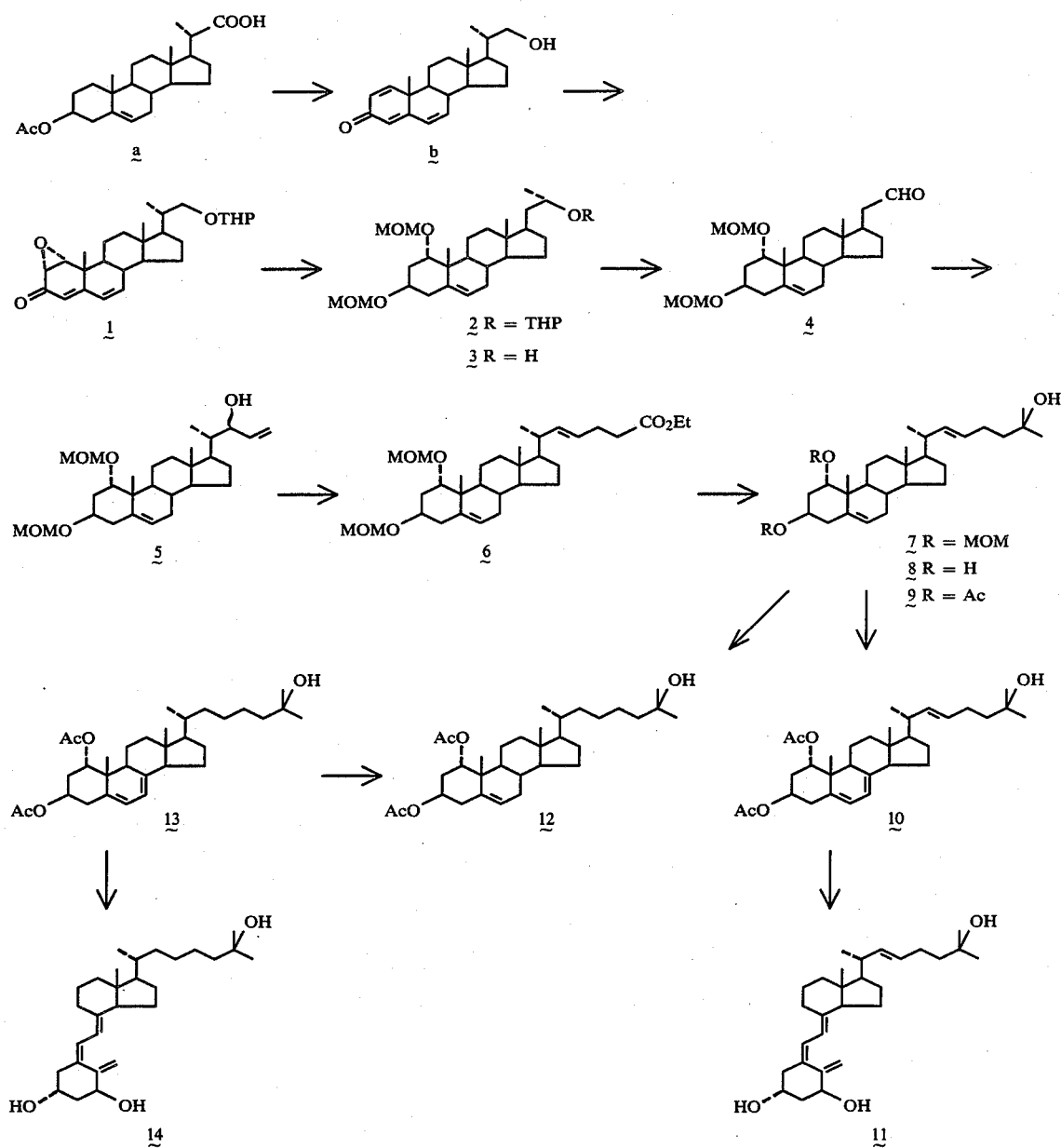

The 5,22-diene (9) was selectively hydrogenated to provide the 5-ene (10) in 92% yield. This compound was converted to 1α,25-dihydroxy-24-homovitamin D₃ (14) via the 5,7-diene (13) as described above in 12% overall yield.

DETAILED DESCRIPTION OF PROCESS

In the following detailed description of the process of this invention melting points were determined with a hot-stage microscope and were uncorrected. $^1$H-NMR spectra were taken with a Hitachi R-24A (60 MHz) in CDCl$_3$ with Me$_4$Si as an internal standard, unless otherwise noted. Mass spectra were obtained with a Shimadzu QP-1000 mass spectrometer at 70 eV. UV spectra were obtained in ethanol solution with a Shimadzu UV-200 double beam spectrophotometer. Column Chromatography was effected using silica gel (E. Merck, Kieselgel 60, 70–230 mesh). Preparative thin layer chromatography was carried out on precoated plates of silica gel (E. Merck, Kieselgel 60 F$_{254}$, 0.25 mm thickness). The usual work-up refers to dilution with water, extraction with an organic solvent indicated in parenthesis, washing the extract to neutrality, drying over anhydrous magnesium sulphate, filtration, and removal of the solvent under reduced pressure. The following abbreviations are used; THP-tetrahydropyranyl; THF-tetrahydrofuran; ether-diethyl ether, MeOH-methanol, MOM-methoxymethyl. Temperatures are in ° centigrade.

22-Hydroxy-23,24-dinorchola-1,4,6-triene-3-one (b)

To a solution of 3β-acetoxydinorcholenic acid (a) (7.0 g, 18.04 mmole) in THF (20 mL) lithium aluminum hydride (3.0 g, 78.95 mmole) was added. This mixture was stirred at 60° C. for 14 h. To this reaction mixture water and ethyl acetate were carefully added. Filtration and removal of the solvent gave the residue (5.2 g). This in dioxane (140 mL) was treated with dichlorodicyanobenzoquinone (11.7g, 51.54 mmole) under reflux for 14 h. After cooling to room temperature the reaction mixture was filtered and the filtrate was evaporated to leave the residue, which was applied to a column of alumina (200 g). Elution with dichloromethane provided the trienone (b) (2.8 g, 47%) mp 156°–157° (ether) UV$\lambda_{max}^{EtOH}$ nm ($\epsilon$): 299 (13000), 252 (9200), 224 (12000), $^1$H-NMR (CDCl$_3$)$\delta$: 0.80 (3H, s, 18-H$_3$), 1.04 (3H, d, J=6 Hz, 21-H$_3$), 1.21 (3H, s, 19-H$_3$), 3.10–3.80 (3H, m, 22-H$_2$ and OH), 5.90–6.40 (4H, m, 2-H, 4-H, 6-H, and 7-H), 7.05 (1H, d, J=10 Hz, 1-H), MS m/z: 326 (M+), 311, 308, 293, 267, 112.

1α,2α-Epoxy-22-tetrahydropyranyloxy-23,24-dinorchola-4,6-dien-3-one (1)

The alcohol (b) (2.7 g, 8.28 mmole) in dichloromethane (50 mL) was treated with dihydropyrane (1.5 mL, 16.42 mmole) and p-toluenesulfonic acid (50 mg) at room temperature for 1 h. The usual work-up (ethyl acetate for extraction) gave a crude product. To a solution of this product in MeOH (70 mL), 30% H$_2$O$_2$ (4.8 mL) and 10% NaOH/MeOH (0.74 mL) were added and this mixture was stirred at room temperature for 14 h. The usual work-up (ethyl acetate for extraction) gave a crude product, which was applied to a column of silica gel (50 g). Elution with benzene-ethyl acetate (100:1) provided the epoxide (1) (1.45 g, 41%): mp 113°–115° (hexane) UV$\lambda_{max}^{EtOH}$ nm ($\epsilon$): 290 (22000), $^1$H-NMR (CDCl$_3$)$\delta$: 0.80 (3H, s, 18-H$_3$), 1.07 (3H, d, J=6 Hz, 21-H$_3$), 1.18 (3H, s, 19-H$_3$), 3.38 (1H, dd, J=4 and 1.5 Hz, 1-H), 3.55 (1H, d, J=4 Hz, 2-H), 3.30–4.10 (4H, m, 22-H$_2$ and THP), 4.50 (1H, m, THP), 5.58 (1H, d, J=1.5 Hz, 4-H), 6.02 (2H, s, 6-H and 7-H), MS m/z: 342 (M+-DHP), 324 (M+-THPOH), 309, 283, 85.

1α,3β-Dimethoxymethoxy-23,24-dinorchol-5-en-22-tetrahydropyranyl ether (2)

Lithium (5.00 g) was added in small portion to liquid ammonia (200 ml) at −78° under argon atmosphere during 30 min. After stirring for 1 hr at −78°, 1α,2α-epoxy-22-tetrapyranyloxy-23,24-dinorchola-4,6-diene-3-one (1) (2.00 g, 4.69 m mol) in dry THF (150 ml) was added dropwise at −78° during 30 min, and this mixture was stirred for 1 hr at −78°. To this reaction mixture, anhydrous NH$_4$Cl (60 g) was added in small portion at −78° during 1 hr. After 1.5 hr the cooling bath was removed and most of the ammonia was removed by bubbling argon. The usual work-up (ether was used as a solvent) gave a crude product. This was treated with chloro-methyl methyl ether (2.0 ml, 26.34 m mol) and N,N-diethylcyclohexylamine (4.6 ml, 24.93 m mol) in dioxane (20 ml) at 45° for 24 hr. The usual work-up (ethyl acetate) gave a crude product, which was applied to a column of silica gel (40 g). Elution with hexane-ethyl acetate (5:1) provided the dimethoxymethyl ether (2) (922 mg, 38%) as an oil. $^1$H-NMR $\delta$ 0.70 (3H, s, 18-H$_3$), 1.02 (3H, s, 19-H$_3$), 1.04 (3H, d, J=6 Hz, 21-H$_3$), 3.34 (3H, s, —O—CH$_3$), 3.37(3H, s, —O—CH$_3$),4.63 (2H, ABq, J=7 Hz, $\Delta$AB=11 Hz, 1α—O—CH$_2$—O—), 4.64 (2H, s, 3β—O—CH$_2$—O—), and 5.50 (1H, m, 6-H).

1α,3β-Dimethoxymethoxy-23,24-dinorchol-5-en-22-ol (3)

The THP ether (2) (922 mg, 1.77 mmol) in THF (8 ml) and MeOH (8 ml) was treated with 2M HCl (1 ml) at room temperature for 2 h. The usual work-up (ethyl acetate) gave a crude product, which was applied to a column of silica gel (40 g). Elution with hexane-ethyl acetate (2:1) gave the alcohol (3) (678 mg, 88%) as an amorphous solid. $^1$H-NMR $\delta$ 0.70 (3H, s, 18-H$_3$), 1.02(3H, s, 19-H$_3$), 1.04 (3H, d, J=6 Hz, 21-H$_3$), 3.34 (3H, s, —O—CH$_3$), 3.38 (3H, s, —O—CH$_3$), 4.65 (2H, ABq, J=7 Hz, $\Delta$AB=11 Hz, 1α—O—CH$_2$—O—), 4.66 (2H, s, 3β—O—CH$_2$—O—), 5.53 (1H, m, 6-H).

1α,3β-Dimethoxymethoxy-23,24-dinorchol-5-en-22-al (4)

To a solution of oxalyl chloride (0.27 ml, 3.09 mmol) in dichloromethane (8 ml) dimethyl sulphoxide (0.44 ml, 6.21 mmol) was added at −78° C. under argon. The mixture was stirred at −78° C. for 10 min. To the solution the alchol (3) (660 mg, 1.51 mmol) in dichloromethane (5 ml) was added at −78° C. After stirring for 15 min, triethylamine (1.89 ml, 13.6 mmol) was added. The mixture was stirred at −78° C. under argon for 5 min, and warmed up to room temperature. The usual work-up (ether) gave a crude product, which was applied to a column of silica gel (30 g). Elution with hexane-ethyl acetate (4:1) gave the aldehyde (4) (607 mg, 92%) as a crystal. mp 71°–72° C. (hexane), $^1$H-NMR $\delta$ 0.74 (3H, s, 18-H$_3$), 1.04 (3H, s, 19-H$_3$), 1.12 (3H, d, J=6 Hz, 21-H$_3$), 3.35 (3H, s, —O—CH$_3$), 3.39 (3H, s, —O—CH$_3$), 3.7 (1H, m, 1β-H), 4.65 (2H, ABq, J=7 Hz, $\Delta$AB=11 Hz, 1α—O—CH$_2$—O—), 4.66 (2H, s, 3β—O—CH—O—), 5.52 (1H, m, 6-H), and 9.61 (1H, d, J=3 Hz, —CHO), Anal. Calcd for C$_{26}$H$_{42}$O$_5$: C, 71:85; H, 9.74. Found: C, 71.71; H, 9.68.

1α,3β-Dimethoxymethoxychola-5,23-dien-22-ol (5)

To magnesium (70 mg, 2.92 mmol) in THF (3 ml) 50% solution of vinyl bromide in THF (0.42 ml, 2.98 mmol) was added. The mixture was stirred at room temperature under argon for 30 min. To the resulting Grignard reagent the aldehyde (4) (595 mg, 1.37 mmol) in THF (6 ml) was added at room temperature. The mixture was stirred at room temperature for 1 h. The usual work-up (ether) gave a crude product, which was applied to a column of silica gel (30 g). Elution with hexane-ethyl acetate (3:1) gave the allylic alcohol (5) (595 mg, 94%) as an amorphous solid. $^1$H-NMR $\delta$: 0.70 (3H, s, 18-H$_3$), 1.02 (3H, s, 19-H$_3$), 3.35 (3H, s, —O—CH$_3$), 3.38 (3H, s, —O—CH$_3$), 3.69 (1H, m, 1β-H), 4.20 (1H, m, 22-H), 4.64 (2H, ABq, J=7 Hz, $\Delta$AB=11 Hz, 1α—O—CHhd 2—O—), 4.65 (2H, s, 3β—O—CH$_2$—O—), 5.52 (1H, m, 6-H), 4.90–6.0 (3H, m, 23-H and 24-H$_2$).

(22E)-1α,3β-Dimethoxymethoxy-27-norcholesta-5,22-dien-26-oic acid ethyl ester (6)

A solution of the allylic alcohol (5) (590 mg, 1.28 mmol), triethyl orthoacetate (1.0 ml, 5.46 l mmol), propionic acid (4 drops), and xylene (8 ml) was refluxed under argon for 2 h. Removal of the solvent under reduced pressure gave the residue, which was applied to a column of silica gel (30 g). Elution with hexane-ethyl acetate (4:1) gave the ester (6) (630 mg, 93%) as an oil. $^1$H-NMR $\delta$: 0.68 (3H, s, 18-H$_3$), 0.97 (3H, d, J=6 Hz, 21-H$_3$), 1.03 (3H, s, 19-H$_3$), 1.24 (3H, t, J=7 Hz, —$CO_2CH_2CH_3$), 3.35 (3H, s, —O—$CH_3$), 3.39 (3H, s, —O—$CH_3$), 3.70 (1H, m, 1β-H), 4.11 (2H, q, J=7 Hz, —$CO_2CH_2CH_3$), 4.64 (2H, ABq, J=7 Hz, ΔAB=11 Hz, 1α—O—$CH_2$—O—), 4.65 (2H, s, 3β—O—$CH_2$—O—), 5.29 (2H, m, 22-H and 23-H), 5.52 (1H, m, 6-H).

If desired the 22E stereo isomer, compound (6), can be readily converted to the 22Z stereo isomer by treatment with iodine. Thus, treatment of compound (6) in ether with a catalytic amount of iodine (2%) of the amount of (6) while under diffuse daylight for 1 hr. results in a trans to cis isomerization which, after HPLC purification, (Zorbax-Sil column, 4.6×25 cm, 6% 2-propanol/hexane) yielded the 22Z stereo isomer.

(22E)-1α,3β-Dimethoxymethoxy-24-homo-cholesta-5,22-diene-25-ol (7)

To a solution of the ester (6) (605 mg, 1.14 mmol) in THF (6 ml) 1M solution of methylmagnesium bromide in THF (4.5 ml, 4.5 mmol) was added at room temperature. The mixture was stirred at room temperature for 1 h. The usual work-up (ether) gave a crude product, which was applied to a column of silica gel (30 g). Elution with hexane-ethyl acetate (3:1) gave the alcohol (7) (548 mg, 93%) as an oil. $^1$H-NMR δ: 0.68 (3H, s, 18-$H_3$), 0.97 (3H, d, J=6 Hz, 21-$H_3$), 1.01 (3H, s, 19-$H_3$), 1.21 (6H, s, 26-$H_3$ and 27-$H_3$), 3.33 (3H, s, —O—$CH_3$), 3.38 (3H, s, —O—$CH_3$), 3.70 (1H, m, 1β-H), 4.64 (2H, ABq, J=7 Hz, ΔAB=11 Hz, 1α—O—$CH_2$—O—), 4.65 (2H, s, 3β—O—$CH_2$—O—), 5.29 (2H, m, 22-H and 23-H), and 5.50 (1H, m, 6-H).

(22E)-24-Homocholesta-5,22-diene-1α,3β,25-triol (8)

A solution of the dimethoxymethyl ether (7) (540 mg, 1.04 mmol) in THF (15 ml) was treated with 6M HCl (3 ml) at 50° C. for 2.5 h. The usual work-up (ethyl acetate) gave a crude product, which was applied to a column of silica gel (20 g). Elution with hexane-ethyl acetate (1:1) gave the triol (8) (428 mg, 95%) as a crystal. mp 164°–166° C. (hexane-ethyl acetate), $^1$H-NMR δ: 0.68 (3H, s, 18-$H_3$), 0.95 (3H, s, J=6 Hz, 21-$H_3$), 1.00 (3H, s, 19-$H_3$), 1.20 (6H, s, 26-$H_3$ and 27-$H_3$), 3.80 (1H, m, 1β-H), 3.92 (1H, m, 3α-H), 5.30 (2H, m, 22-H and b 23-H), and 5.53 (1H, m, 6-H).

(22E)-1α,3β-Diacetoxy-25-hydroxy-24-homocholesta-5,22-diene (9)

A solution of the triol (8) (395 mg, 0.919 mmol) in pyridine (2 ml) was treated with acetic anhydride (1 ml) at room temperature for 16 h. The usual work-up (ethyl acetate) gave a crude product, which was applied to a column of silica gel (20 g). Elution with hexane-ethyl acetate (2:1) gave the diacetate (9) (361 mg, 77%) as an oil. $^1$H-NMR δ: 0.67 (3H, s, 18-$H_3$), 0.97 (3H, d, J=6 Hz, 21-$H_3$), 1.07 (3H, s, 19-$H_3$), 1.21 (6H, s, 26-$H_3$ and 27-$H_3$), 2.01 (3H, s, acetyl), 2.04 (3H, s, acetyl), 4.98 (1H, m, 3α-H), 5.05 (1H, m, 1β-H), 5.31 (2H, m, 22-H and 23-H), and 5.52 (1H, m, 6-H).

(22E)-1α,3β-Diacetoxy-25-hydroxy-24-homocholesta-5,7,22-triene (10)

A solution of the 5-ene (9) (51 mg, 0.0992 mmol) and N-bromo-succinimide (21 mg, 0.118 mmol) in carbontetrachloride (3 ml) was refluxed under argon for 20 min. After the mixture had been cooled to 0° C., the resulting precipitate was filtered off. The filtrate was concentrated below 40° C. to leave the residue. This in THF (5 ml) was treated with a catalytic amount of tetra-n-butylammonium bromide at room temperature for 50 min. Then, the mixture was treated with a solution of tetra-n-butylammonium fluoride in THF (3.5 ml, 3.5 mmol) at room temperature for 30 min. The usual work-up (ethyl acetate) gave a crude product, which was submitted to preparative thin layer chromatography (hexane-ethyl acetate, 4:1, developed five times). The band of Rf value 0.48 was scraped off and eluted with ethyl acetate. Removal of the solvent provided the 5,7-diene (10) 12.5 mg, 24%), UVλ$_{max}^{EtOH}$: 293, 282, and 271.

1α,25-Dihydroxy-22E-dehydro-24-homovitamin $D_3$ (11)

A solution of the 5,7-diene (10) (7.3 mg, 0.0143 mmol) in benzene (90 ml) and ethanol (40 ml) was irradiated with with a medium pressure mercury lamp through a Vycol filter at 0° C. under argon for 5 min. The reaction mixture was refluxed under argon for 1 h. Removal of the solvent under reduced pressure gave a crude product, which was submitted to preparative thin layer chromatography (hexane-ethyl acetate, 4:1, developed five times). The band of Rf value 0.38 was scraped off and eluted with ethyl acetate. Removal of the solvent gave the vitamin $D_3$ diacetate (1.8 mg, 25%). The band of Rf value 0.43 was scraped off and eluted with ethyl acetate. Removal of the solvent recovered the 5,7-diene (10) (2.1 mg, 29%).

The vitamin $D_3$ diacetate (1.8 mg, 2.15 μmol) in THF (4 ml) was treated with 5% KOH/MeOH (1 ml) at room temperature for 20 min. The usual work-up (ethyl acetate) gave a crude product, which was submitted to preparative thin layer chromatography (hexane-ethyl acetate, 1:2, developed three times). The band of Rf value 0.43 was scraped off and eluted with ethyl acetate. Removal of the solvent gave the vitamin $D_3$ analogue (11) (1.4 mg, 90%). The purity of the product (11) was determined as 100% by high performance liquid chromatography (a Shimadzu LC-3A; column, Zorbax ZIL normal phase, 4.6 mm i.d.×15 cm; solvent, MeOH—$CH_2Cl_2$, 1:49; flow rate, 3 ml/min; retention time, 11.5 min). The vitamin $D_3$ analogue (11) had the following spectral data; UVλ$_{max}^{EtOH}$: 265 nm, λ$_{min}^{EtOH}$: 228 nm, MS m/z: 428 (M+), 410, 392 (base peak), 374, 287, 269, 251, 152, 134, 123, 59, $^1$H-NMR (360 MHz) δ: 0.55 (3H, s, 18-$H_3$), 1.02 (3H, d, J=6.6 Hz, 21-$H_3$), 1.22 (6H, s, 26-$H_3$ and 27-$H_3$), 2.32 (1H, dd, J=13.2 and 6.7 Hz), 2.60 (1H, dd, J=13.0 and 3.0 Hz), 2.83 (1H, dd, J=12.0 and 3.0 Hz), 4.23 (1H, m, W½=18.4 Hz, 3α-H), 4.43 (1H, m, W½=16.9 Hz, 1β-H), 5.00 (1H, bs, W½=3.2 Hz, 19-H), 5.30 (1H, dd, J=15.0 and 7.1 Hz, 22-H or 23-H), 5.33 (1H, bs, W½=3.2 Hz, 19-H), 5.37 (1H, dd, J=15.0 and 5.8 Hz, 22-H or 23-H), 6.01 (1H, d, J=11.0 Hz, 7-H), 6.32 (1H, d, J=11.0 Hz, 6-H).

1α,3β-Diacetoxy-24-homocholest-5-en-25-ol (12)

A mixture of the 5,22-diene (9) (40 mg, 0.0778 mmol) and 10% Pd-C (4 mg) in ethyl acetate (2 ml) was stirred at room temperature under hydrogen for 3 h. The Pd catalyst was filtered off and the filtrate was concentrated to leave the residue, which was applied to a column of silica gel (5 g). Elution with hexane-ethyl acetate (4:1) gave the 5-ene (12) (37 mg, 92%) as an oil. $^1$H-NMR δ: 0.66 (3H, s, 18-$H_3$), 1.08 (3H, s, 19-$H_3$), 1.20 (6H, s, 26-$H_3$ and 27-$H_3$), 2.02 (3H, s, acetyl), 2.05 (3H, s, acetyl), 4.97 (1H, m, 3α-H), 5.07 (1H, m, 1β-H), 5.53 (1H, m, 6-H).

1α,3β-Diacetoxy-24-homocholesta-5,7-dien-25-ol (13)

The 5-ene (12) (19 mg, 0.037 mmol) was converted, as described for (10), to the 5,7-diene (13) (5.8 mg, 31%). UV$\lambda_{max}^{EtOH}$: 293, 282, 271 nm 1α,25-Dihydroxy-24-homovitamin D$_3$ (14)

The 5,7-diene (13) (5.8 mg, 0.0113 mmol) was converted, as described for (11), to the vitamin D$_3$ analogue (14) (890 μg, 19%). The retention time of (14) under the above-described HPLC condition was 11.0 min. UV$\lambda_{max}^{EtOH}$: 265 nm, $\lambda_{min}^{EtOH}$: 228 nm. MS m/z 430 (M+), 412, 394 (base peak, 376, 287, 269, 251, 152, 134, 59.

If desired, the compounds of this invention can be readily obtained in crystalline form by crystallization from suitable solvents, e.g. hexane, ethers, alcohols, or mixtures thereof as will be apparent to those skilled in the art.

Biological Activity

Bone calcium mobilization activities of 1α,25-(OH)$_2$-24-homo-D$_3$ compounds

Bone calcium mobilization activity was assayed by measuring the rise in serum calcium levels in response to the compound administered. Male, weanling rats (Holtzman Co., Madison, WI) were fed a low-calcium, vitamin D deficient diet (Suda et al, J. Nutr. 100 1049–1050, 1970) and water ad libitum for 3 weeks. The rats were then divided into three groups of 5–6 rats each and were given intrajugularly either 1,25-(OH)$_2$D$_3$ or the test compound dissolved in 0.05 ml of 95% ethanol. Rats in the control group were given 0.05 ml ethanol vehicle in the same manner. Eighteen hours after the dose, the rats were killed and their blood was collected and centrifuged to obtain serum. Serum calcium concentrations were determined with an atomic absorption spectrometer Model 403 (Perkin-Elmer Co., Norwalk, Conn.) in presence of 0.1% lanthanum chloride.

Results obtained are shown in the following Table:

TABLE 1

| | Increase of serum calcium concentration in response to a compound administered | | |
|---|---|---|---|
| | Compound Administered | Amount Administered (pmol/rat) | Serum calcium Concentration (mg/100 ml) |
| Exp. I | Ethanol | — | 3.6 ± 0.3[a]* |
| | 1α,25-(OH)$_2$D$_3$ | 650 | 4.9 ± 0.2[b] |
| | 1α,25-(OH)$_2$-24-homo-D$_3$ | 650 | 4.4 ± 0.2[b] |
| Exp. II | Ethanol | — | 4.2 + 0.1[c] |
| | 1α,25-(OH)$_2$D$_3$ | 325 | 5.0 + 0.5[d] |
| | 1α,25-(OH)$_2$-22E-dehydro-24-homo-D$_3$ | 650 | 5.0 ± 0.5[d] |

*Standard deviation from the means significantly different [b] from [a] and [d] from [c] p 0.001

It can be concluded from the foregoing data that in the vitamin D responsive systems of vitamin D-deficient animals the compounds of this invention exhibited the same activity as 1α,25-hydroxyvitamin D$_3$, the circulating hormonal form of the vitamin, although, in the case of the 22-dehydro derivative the dosage was significantly higher.

It has been recently discovered that 1α,25-dihydroxyvitamin D$_3$ (1α,25-(OH)$_2$D$_3$) and its structural analog 1α-hydroxyvitamin D$_3$ (1α-OH-D$_3$), in addition to their well-established calcemic action referred to above, also express potent anti-cancer activity. Specifically, it was shown that the above-named compounds were effective in causing differentiation of malignant human cells, such as leukemia cells in culture, to non-malignant macrophages, and the anti-cancer activity on cells in vitro could be correlated with beneficial effects in vivo by showing that the administration of these compounds extended the life span of leukemic mice (compared to controls) and markedly improved the condition of human leukemia patients. Based on these observations, 1α-hydroxylated vitamin D compounds have been proposed as therapeutic agents for the treatment of leukemoid diseases (Suda et al., supra).

Although these known 1α-hydroxyvitamin D compounds tested by Suda et al. (supra), namely 1α-hydroxyvitamin D$_3$ (1α-D$_3$) and 1α,25-dihydroxyvitamin D$_3$ (1α,25-(OH)$_2$D$_3$), are indeed highly effective in causing differentiation of leukemic cells, a serious disadvantage to their use as antileukemic agents is the inherent, and hence unavoidable high calcemic activity of these substances. Thus, 1α,25-(OH)$_2$D$_3$, the most potent vitamin-derived antileukemic agent known thus far, is also the most potent calcemic agent, and the antileukemic potency of 1α-OH-D$_3$ is likewise correlated with high calcemic activity. The administration of these compounds, at the dosage level where they are effective as antileukemic drugs (e.g. 1 μg/day as specified in the examples of the Suda et al. patent), would necessarily produce elevated, potentially excessive, calcium levels with attendant serious medical complications, particularly in patients already suffering from debilitating disease. Because of the high intrinsic potency of the known 1α-hydroxyvitamin D compounds in raising calcium levels, their use as antileukemic agents may be precluded.

A preferred method of treatment of malignant disease states clearly would be the administration of compounds characterized by a high antileukemic to calcemic activity ratio, that is, of compounds exhibiting an enhanced potency in causing differentiation of leukemic cells as compared to their potency in raising serum calcium levels.

The compounds of the present invention offer such preferred method in that they are more active than 1α,25-dihydroxyvitamin D$_3$ (1α,25-(OH)$_2$D$_3$) in antineoplastic activity as measured by leukemia cell differentiation, while being no more active, or somewhat less active than 1α,25-dihydroxyvitamin D$_3$ in their effect on calcium metabolism. Because of this unique and unexpected combination of properties, the novel side-chain homovitamin D compounds of this invention represent superior and preferred agents for the treatment of leukemias and other neoplastic diseases.

When administered to human promyelocytic leukemia cells (HL-60 cells) grown in culture, the side-chain homovitamin D compounds of this invention induce the differentiation of these cells to macrophages (monocytes). In several standard assays for measuring differentiation activity, such compounds were shown to be more effective than 1α,25-(OH)$_2$D$_3$, the most active vitamin D derivative known thus far. These assays were performed as follows:

Assay of homovitamin D compounds for differentiation activity

The human promyelocytic leukemia cell line (HL-60) was maintained in suspension culture in RPM1 1640 medium (Gibco, Grand Island, NY) supplemented with 10% (v/v) heat inactivated fetal calf serum, 100 μg/ml penicillin, 100 μg/ml streptomycin and 0.25 μg/ml fungizone. Cells were cultured in a humidified atmosphere with 5% $CO_2$. Cell viability was assessed by standard assays, e.g. trypan blue exclusion. Morphological evaluations were done on Wright stained slide preparations.

Cells were seeded at $1.5-2 \times 10^5$ cells/ml in 10 ml of medium in tissue culture dishes. After 20 hr, duplicate dishes were then treated with each of the test compounds (i.e. 1α,25-(OH)Hd 2D$_3$, and compounds I, II, III and IV) at various concentrations as indicated in the tables below. The test compounds were added as solutions in 100% ethanol so that the total ethanol concentration in each culture dish did not exceed 0.2%. Control cultures were treated with the same concentration of ethanol. After four days (96 hr) of incubation with test compounds, the cells were harvested from these culture dishes and cell number and viability were determined. The extent of differentiation induced by the tested vitamin D derivatives was expressed as the percentage of cells that exhibit funchonal and enzymatic markers characteristic of monocytes. The two markers assayed were (a) the ability of the cells to phagocytize dead yeast, and (b) the ability of the cells to produce superoxide (reduce nitrotetrazalium blue) when stimulated with pharbol esters.

(a) Phagocytosis Assay for Differentiation Activity

The harvested cells were resuspended in RPM1 medium containing 20% AB serum and 20% fetal calf serum, to give a preparation containing $2 \times 10^6$ cells/ml. To 0.5 ml ($10^6$ cells) of the above cell suspension was then added 0.5 ml of a suspension (in phosphate-buffered saline) of heat-killed saccharomyces cerevisiae cells ($1 \times 10^8$ cells) which had been stained with trypan blue. After incubation of this mixture for 1 hr at 37° C., the number of phagocytic cells was counted (as determined by the trypan blue stained yeast appearing intracellularly) and expressed as a percent of the total viable cells present. This "% phagocytic cells" indicates the percent of differentiation induced by the test compounds. Results are summarized in Table 1 below.

The results in Table 1 show that the 24-homo compounds have very similar differentiation activity, and are significantly more potent than 1,25-(OH)$_2$D$_3$. At all concentrations, the homo compounds achieve a greater degree of differentiation of the leukemia cells than 1α,25-(OH)$_2$D$_3$, the most active compound known thus far. For example, at a concentration of $10^{-8}$ molar the homo compounds achieve a differentiation of 70%, whereas 1,25-(OH)$_2$D$_3$ at the same concentration gives only about 47% differentiated cells. To achieve an approximately 50% differentiation requires a concentration of $1 \times 10^{-9}$M of the homo compounds, but about $1 \times 10^{-8}$M of 1α,25-(OH)$_2$D$_3$, i.e. a difference in potency of about 10-fold.

(b) NBT-Reduction Assay for Differentiation

This assay depends on the ability of monocyte-like leukemia cells to reduce the nitroblue tetrazolium (NBT) reagent to a black-blue precipitate (formazan) when stimulated by phorbol esters. The assay was performed according to the general procedure given by Yen et al (J. Cellular Physiol. 118, 277 (1984)). The cells were harvested as above and then suspended in RPMI medium; to 0.2 ml of this suspension (containing about $1.4 \times 10^6$ cells/ml) was added 0.2 ml of the nitroblue tetrazolium (NBT) reagent. (The NBT reagent was prepared by mixing a solution containing 50 mg of nitroblue tetrazolium in 50 ml of phosphate-buffered saline with 10 microliters of an acetone/water (1:1) solution containing 0.5 mg/ml of 4β-phorbol-12-myristate-13-acetate). After standing in a water bath for 30 min, the differentiated cells (i.e. the cells showing formazan blue deposits indicative of NBT reduction) were counted with a hemocytometer and expressed as the percent of total viable cells present. The results of this assay are shown in Table 2 below.

TABLE 2

Percent of cells in HL-60 cell cultures exhibiting nitroblue tetrazolium (NBT) reduction activity after treatment with Vitamin D Compounds at various concentrations

| Compound Administered | Concentration (moles/liter) | | | | | | |
|---|---|---|---|---|---|---|---|
| | $0^{a,b}$ | $3 \times 10^{-10}$ | $5 \times 10^{-10}$ | $1 \times 10^{-9b}$ | $1 \times 10^{-8b}$ | $1 \times 10^{-7b}$ | $3 \times 10^{-7}$ |
| 1,25-(OH)$_2$D$_3$ | 10 ± 1.5 | 15 | 27 | 31 ± 4 | 45 ± 4 | 69 ± 7 | 65 |
| Compound I* | 10 ± 1.5 | 33 | 39 | 46 ± 4 | 72 ± 1 | 79 ± 5 | 77 |
| Compounds II* | 10 ± 1.5 | 33 | 45 | 52 ± 5 | 71 ± 1 | 78 ± 5 | 79 |

$^a$Control level; cell cultures treated with solvent ethanol only.
$^b$Data represent the mean ± SEM of three separate experiments, each assayed in duplicate.
*Compound I = 1α,25-dihydroxy-24-homovitamin D$_3$
Compound II = 1α,25-dihydroxy-22E-dehydro-24-homovitamin D$_3$ The results shown in Table 2 again establish that the 24-homo compounds tested are more active than 1α,25-(OH)$_2$D$_3$ in inducing the differentiation of human myeloid leukemia cells to normal cells, in vitro and that, as in the previous assay (Table 1) all the homo compounds exhibit very similar potency. To achieve 60% differenti-

TABLE 1

Percent phagocytic (differentiated) cells produced in HL-60 cell cultures treated with vitamin D compounds at various concentrations

| Compound Administered | Concentration (moles/liter) | | | | | | |
|---|---|---|---|---|---|---|---|
| | $0^{a,b}$ | $3 \times 10^{-10}$ | $5 \times 10^{-10}$ | $1 \times 10^{-9b}$ | $1 \times 10^{-8b}$ | $1 \times 10^{-7b}$ | $3 \times 10^{-7}$ |
| 1,25-(OH)$_2$D$_3$ | 10 ± 1.5 | 17 | 23 | 28 ± 4 | 47 ± 1 | 67 ± 6 | 69 |
| Compound I* | 10 ± 1.5 | 29 | 38 | 47 ± 6 | 69 ± 3 | 77 ± 1 | 78 |
| Compound II* | 10 ± 1.5 | 31 | 48 | 51 ± 4 | 69 ± 0.5 | 77 ± 1 | 78 |

$^a$Control level; cell cultures were treated with solvent ethanol only.
$^b$Results tabulated in these columns represent the mean ± SEM of three different experiments, each done in duplicate.
*Compound I - 1α,25-dihydroxy-24-homovitamin D$_3$
Compound II - 1α,25-dihydroxy-22E-dehydro-24-homovitamin D$_3$ ation of the leukemic cells as measured by this NBT reduction assay, requires a concentration of $2\times10^{-9}$M of the homo compounds; to achieve the same degree of differentiation with $1\alpha,25\text{-}(OH)_2D_3$ requires a concentration of $3.5\times10^{-8}$M-a 17-fold difference in potency.

Thus, both of the above assays confirm the high potency of the 24-homovitamin D compounds in inducing the differentiation of leukemic cells. In addition, the above results show that in this differentiation activity these homovitamin D compounds are 10–20 times more potent than $1\alpha,25\text{-}(OH)_2D_3$.

The compounds of this invention may be readily administered in sterile parenteral solutions by injection or intravenously or by alimentary canal in the form of oral dosages, or by suppository or even transcutaneously. Doses of from about 0.1 μg to about 2.5 μg per day are effective in obtaining the physiological calcium balance responses characteristic of vitamin D-like activity with maintenance dosage of from about 0.1 μg to about 0.5 μg being suitable. For the treatment of human leukemia the homovitamin D compounds are administered to subjects in dosages sufficient to induce the differentiation of leukemia cells to macrophages. Suitable dosage amounts are from 0.2 μg to 5 μg per day. It will be evident that for any application the dosages can be adjusted according to the needs of a subejct in a particular physiological or disease state being treated, or to the response or condition of the subject as well as other factors known to those skilled in the art in the therapeutic use of such medicinal agents.

Dosage forms of the compounds can be prepared by combining them with a non-toxic pharmaceutically acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

We claim:

1. Compounds having the formula

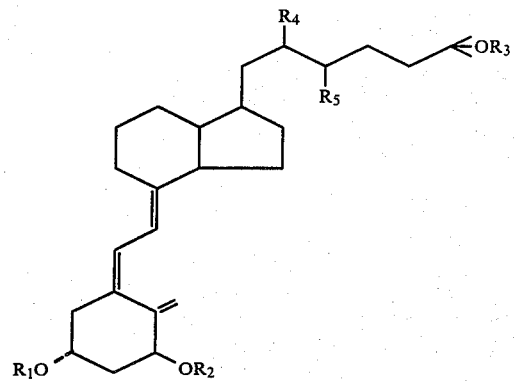

where $R_1$, $R_2$ and $R_3$ are each selected from the group consisting of hydrogen, an acyl group having from 1 to about 4 carbon atoms and benzoyl and $R_4$ and $R_5$ each represent hydrogen atoms or taken together form a carbon to carbon double bond.

2. A compound according to claim 1 wherein $R_1$, $R_2$ and $R_3$ are hydrogen and $R_4$ and $R_5$ are hydrogen atoms.

3. The compound of claim 2 in crystalline form.

4. A composition comprising the compound of claim 2 and a pharmaceutically acceptable excipient.

5. A compound according to claim 2 wherein the Δ22 bond is in the E configuration.

6. A compound according to claim 2 wherein the Δ22 bond is in the Z configuration.

7. A compound according to claim 1 wherein $R_1$, $R_2$ and $R_3$ are hydrogen and $R_4$ and $R_5$ together represent a carbon to carbon double bond.

8. The compound of claim 7 in crystalline form.

9. Compounds having the formula

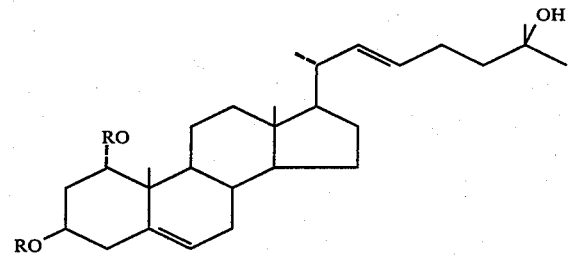

where R is selected from the group consisting of hydrogen, an acyl group having from 1 to about 4 carbon atoms, benzoyl and methoxymethyl.

10. Compounds having the formula

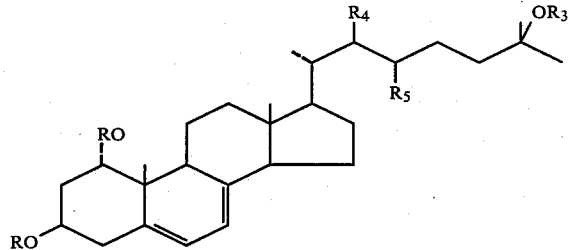

where R is selected from the group consisting of an acyl group having from about 1 to about 4 carbon atoms and benzoyl and $R_4$ and $R_5$ represent hydrogen atoms or taken together form a carbon to carbon double bond.

* * * * *